(12) United States Patent
Doyle et al.

(10) Patent No.: US 7,361,497 B2
(45) Date of Patent: Apr. 22, 2008

(54) PROBIOTIC BACTERIA

(75) Inventors: Michael P. Doyle, Peach Tree City, GA (US); Michelle D. Danyluk, Davis, CA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 326 days.

(21) Appl. No.: 10/531,796

(22) PCT Filed: Oct. 16, 2003

(86) PCT No.: PCT/US03/32706

§ 371 (c)(1), (2), (4) Date: Apr. 18, 2005

(87) PCT Pub. No.: WO2004/034989

PCT Pub. Date: Apr. 29, 2004

(65) Prior Publication Data

US 2006/0034814 A1    Feb. 16, 2006

Related U.S. Application Data

(60) Provisional application No. 60/419,495, filed on Oct. 18, 2002.

(51) Int. Cl.
  *C12N 1/20* (2006.01)
  *C12N 1/00* (2006.01)
  *A01N 63/00* (2006.01)

(52) U.S. Cl. .................. 435/252.1; 435/252.4; 435/822; 424/93.1; 424/93.4

(58) Field of Classification Search .............. 435/252.1, 435/252.4, 822; 424/93.1, 93.4
See application file for complete search history.

(56) References Cited

U.S. PATENT DOCUMENTS

| 5,478,557 A | 12/1995 | Nisbet et al. |
| 5,951,977 A | 9/1999 | Nisbet et al. |

OTHER PUBLICATIONS

PCT International Search Report for PCT/US2003/032706 completed by the U.S. Searching Authority on Mar. 8, 2004.

*Primary Examiner*—Vera Afremova
(74) *Attorney, Agent, or Firm*—Barnes & Thornburg LLP

(57) ABSTRACT

Strains of probiotic bacteria, their isolation, characteristics and methods of use to prevent or treat carriage by a food production animal of *Salmonella* that causes human salmonellosis are provided. Methods for isolating and characterizing the probiotic bacteria are also provided. The present invention further provides methods for using the probiotic bacteria to prevent or treat *Salmonella* strains that cause human salmonellosis found in food production animals.

7 Claims, 5 Drawing Sheets

PROBIOTIC BACTERIA

CROSS REFERENCE TO RELATED APPLICATIONS

This application is a U.S. national counterpart application of international application serial No. PCT/US2003/032706 filed Oct. 16, 2003, which claims priority to U.S. Provisional Patent Application No. 60/419,495 filed Oct. 18, 2002. The entirety of which is hereby incorporated by reference.

FIELD OF THE INVENTION

This invention relates generally to the control of pathogenic bacteria in animals raised for human consumption and more particularly to the control of *Salmonella enterica* serovar *Typhimurium* DT104 and *Salmonella enterica* serovar Newport by administering probiotic bacteria to the animals.

BACKGROUND OF THE INVENTION

*Salmonella* spp. are widespread with in the environment. Their primary habitat is the intestinal tracts of birds, reptiles, animals (especially those on the farm), humans, and occasionally insects. They may also be found in other parts of the body from time to time, for example in the spleen, liver, bile, mesenteric and portal lymph nodes, diaphragm, and pillar in slaughterhouse pigs. Jay, J. M., *Modern Food Microbiology*, 6th ed. Aspen Publishers, Gaithersburg, Md. (2000).

Serovars that cause human salmonellosis are most often found in foods of animal origin, such as pork and poultry meats, and dairy products. Oosterom, J., *Int. J. Food Microbiol.* 12:41-52 (1991). The persistence of salmonellae in slaughterhouses and meat processing facilities continues due to the exposure of livestock to environmental sources of contamination, contaminated feeds, and parental transmission of infection. The feces of infected humans and animals contaminate water sources, which subsequently infect farm animals, then contaminate meat during slaughter, and subsequently infect humans, beginning the cycle anew. This cycle is augmented by the practice of international shipping of animal products and feed, which has lead to the worldwide distribution of salmonellosis.

In the 1980s, surveillance data of cattle and human isolates indicate that *Salmonella enterica* serovar *Typhimurium* DT104 emerged worldwide. *S. Typhimurium* DT104 typically is resistant to the antibiotics ampicillin, chloramphenicol, streptomycin, sulphonamides and teracycline (R-type ACSSuT). Threlfall, E. J. et al., *Vet. Rec.* 134:577 (1994). Currently, data suggest that a multi-resistant *Salmonella enterica* serovar Newport is emerging in the United States. S. Newport typically is resistant to at least nine antibiotics. Recent studies revealed that 3.5% of retail ground beef was positive for *Salmonella* spp. of which 35.6% was *S. Typhimurium* DT104. Zhao T. et al., *J. Food Prot.* 65:403-407 (2002). Between January and April 2002, a five-state outbreak of S. Newport occurred. Exposure to raw or undercooked ground beef was implicated as the vehicle of transmission. Cattle are thought to be a primary reservoir through which both these multi-resistant pathogens can enter the food supply.

Clinical symptoms of *S. Typhimurium* DT104 in humans include diarrhea, fever headache, nausea, vomiting and abdominal pain. One-fourth of patients infected in a case-control study had bloody diarrhea, 41% of patients required hospitalization, and 3% of patients died. This is much higher than the case-fatality rate associated for non-typhoid *Salmonella* infections, which other than for DT104, is approximately 0.1%. Aldina, J. E. et al., *J. Am. Vet. Med. Assoc.* 214:790-798 (1999).

Surveys of feedlot cattle in the United States done in 1998 revealed that 38% of feedlots were *Salmonella* spp. positive, and 5.5% of all fecal samples collected were positive for *Salmonella* spp. *S. Typhimurium* DT104 was detected in 2.6% of the feedlots, and 2.9% of the positive fecal samples. Fedorka-Cray, P. J. et al., *J. Food Prot.* 61:525-530 (1998). A similar study conducted on beef cattle in 2000 revealed that 11.2% of all operations tested positive for *Salmonella* spp., and 1.4% of all fecal samples were positive. Dargatz, D. A. et al., *J. Food Prot.* 63:1648-1653 (2000). There are clear associations between *S. Typhimurium* DT104 infection in food production animals and humans. Davis, A. et al., *Communicable Disease Report CDR Rev.* 6:159-162 (1996).

SUMMARY OF THE INVENTION

Strains of probiotic bacteria, their isolation, characteristics and methods of use to prevent or treat carriage by a food production animal of *Salmonella* that causes human salmonellosis are provided. A non-limiting example of *Salmonella* strains that cause human salmonellosis are *Salmonella enterica Typhimurium* DT104 or Newport. By "probiotic" it is meant bacteria having the property of preventing establishment of *Salmonella* in a food production animal previously administered an effective dose of said probiotic bacteria. Strains of probiotic bacteria that inhibit the growth of *Salmonella* strains that cause human salmonellosis can be strains of *E. coli* and *Bacillus circulans*.

The present invention also provides a method for preventing the carriage by a food production animal of *Salmonella* strains that cause human salmonellosis. The method comprises the step of administering an effective amount of a strain or combination of strains of probiotic bacteria to the food production animal prior to exposure to *Salmonella* strains that cause human salmonellosis.

The invention further provides a method for reducing or eliminating from a food source animal *Salmonella* strains that cause human salmonellosis by administering an effective amount of a strain or combination of strains of probiotic bacteria. The method is useful to maintain herds or flocks of animals free of *Salmonella* strains that cause human salmonellosis and reduce carriage and fecal shedding of *Salmonella* strains that cause human salmonellosis prior to slaughter.

The administration of probiotic bacteria is accomplished by feeding a feed supplement or additive which comprises an effective amount of probiotic bacteria, or by supplying a water treatment additive or inoculum to the animals' drinking water. The invention therefore provides a feed supplement composition comprising probiotic bacteria and a water additive comprising probiotic bacteria.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE INVENTION

Figure 1A:
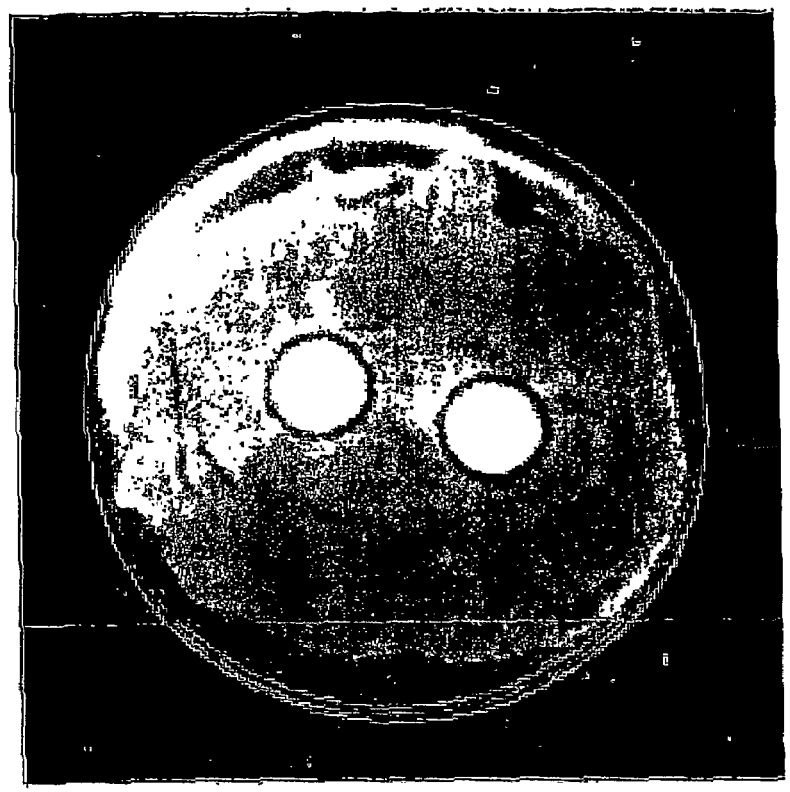
FIG. 1A is a photograph of a paper disk assay showing the zones of inhibition of *S. Typhimurium* DT104 by isolate 36-1 on TSA agar.

Strains of probiotic bacteria, their isolation, characteristics and methods of use to prevent or treat carriage by a food production animal of *Salmonella* that causes human salmonellosis are provided. The probiotic bacteria and methods of the present invention are especially effective for preventing and or treating carriage of *Salmonella* strains that cause human salmonellosis and have multiple antibiotic resistance. A non-limiting example of *Salmonella* strains that cause human salmonellosis are *Salmonella enterica Typhimurium* DT104 or Newport.

"Food production animal" is used herein to describe any mammal or avian that is prepared and used for human consumption. A food production animal can be, but not limited to, a ruminant animal such as beef and dairy cattle, pigs, lamb, chicken, turkey or any other fowl.

"Probiotic" is used herein as an adjective to describe bacteria isolated from a natural source and having the property of inhibiting the growth of *Salmonella* strains that cause human salmonellosis. The test of an inhibition used herein was an in vitro test on solid medium in which culture supernatants of candidate isolated bacteria were observed for their property of inhibiting *Salmonella enterica Typhimurium* DT104 or Newport growth when applied to the surface of the solid medium. Typically, a paper disc impregnated with the culture supernatant of a candidate strain was placed on the surface of an agar plate seeded with either *Salmonella enterica Typhimurium* DT104 or Newport. Probiotic bacterial supernatants caused a ring of clear agar or of reduced growth density indicating inhibition of *Salmonella enterica Typhimurium* DT104 or Newport in the vicinity of the disc. There are other tests for inhibition which are available or could be devised, including direct growth competition tests, in vitro or in vivo which can generate a panel of probiotic bacteria similar to that described herein. The bacterial strains identified by any such test are within the category of probiotic bacteria, as the term is used herein.

The term "dominant probiotic" is applied to probiotic bacteria which persist in, and are re-isolatable from an animal to which the bacteria have been administered. For example, bovine calves can be fed a mixture of probiotic strains, then from a variety of tissues, digestive contents and feces are sampled 26 days post-inoculation. Recovered strains are designated dominant probiotic strains. Other criteria can be employed, including shorter or longer time periods between inoculation and sampling. It is advisable to choose a time period sufficiently long that persistence of dominant probiotic strains can provide useful reduction of the amount of *Salmonella* strains that cause human salmonellosis carried by the animal.

Isolation of probiotic bacteria can be carried out by those of ordinary skill in the art, following the principles and procedures described herein. Of 1097 colonies isolated from cattle feces and tissues, six gram-positive isolates and 24 gram-negative isolates were identified as probiotic bacteria. Eight of the isolates, 31-6, 47-10, 50-10, 58-9, 59-9 small, 59-9 big, 71-8 and 76-9 were better at inhibiting *Salmonella enterica Typhimurium* DT104 or Newport. Therefore, the testing of similar numbers of independent isolates is reasonably likely to successfully yield probiotic bacteria. Probiotic bacteria isolates 31-6, 76-9 and 58-9 have been deposited with the American Type Culture Collection (ATCC), 1080 University Boulevard, Manassas, Va. 20110-2209, under the terms of the Budapest Treaty, on Oct. 23, 2003, and have been accorded the ATCC designation numbers PTA-5616, PTA-5615, and PTA-5614, respectively. The deposit will be maintained in the ATCC depository, which is a public depository, for a period of 30 years, or 5 years after the most recent request, or for the effective life of a patent, whichever is longer, and will be replaced if the deposit becomes depleted or nonviable during that period. Samples of the deposit will become available to the public and all restrictions imposed on access to the deposit will be removed upon grant of a patent on this application.

The probiotic bacteria can be any type of bacteria and may not necessarily be a different strain of *Salmonella*. For example, of the probiotic bacteria described herein, 22 of the isolates were identified as *E. coli*, and 7 were identified as *Bacillus circulans*. Administration of probiotic bacteria can be accomplished by any method likely to introduce the organisms into the digestive tract. The bacteria can be mixed with a carrier and applied to liquid or solid feed or to drinking water. The carrier material should be non-toxic to the bacteria and the animal. Preferably, the carrier contains an ingredient that promotes viability of the bacteria during storage. The bacteria can also be formulated as an inoculant paste to be directly injected into an animal's mouth. The formulation can include added ingredients to improve palatability, improve shelf-life, impart nutritional benefits, and the like. If a reproducible and measured dose is desired, the bacteria can be administered by a rumen cannula. The amount of probiotic bacteria to be administered is governed by factors affecting efficacy. When administered in feed or drinking water the dosage can be spread over a period of days or even weeks. The cumulative effect of lower doses administered over several days can be greater than a single larger dose thereof. By monitoring the numbers of *Salmonella* strains that cause human salmonellosis in feces before, during and after administration of dominant probiotic bacteria, those skilled in the art can readily ascertain the dosage level needed to reduce the amount of *Salmonella* strains that cause human salmonellosis carried by the animals. One or more strains of dominant probiotic bacteria can be administered together. A combination of strains can be advantageous because individual animals may differ as to the strain which is most persistent in a given individual.

Probiotic bacteria can be administered as a preventive, to prevent animals not presently carrying *Salmonella* strains that cause human salmonellosis from acquiring the strains by exposure to other animals or environments where the strains are present. Young and mature food production animals about to be transferred to a new location, such as a feed lot, are attractive candidates for preventive administration.

Treatment of animals carrying *Salmonella* strains that cause human salmonellosis can be accomplished to reduce or eliminate the amount of the strains carried by the animals, by administering probiotic bacteria to animals infected with *Salmonella* strains that cause human salmonellosis. Animals known to be shedding the strains in feces, or those raised where the strains are known to exist are suitable candidates for treatment with probiotic bacteria.

The methods for administering probiotic bacteria are essentially the same, whether for prevention or treatment. Therefore, the need to first determine whether the undesired *Salmonella* strains are being carried by the animals is removed. By routinely administering an effective dose to all the animals of a herd, the risk of contamination by the undesired *Salmonella* strains can be substantially reduced or eliminated by a combination of prevention and treatment.

The foregoing and other aspects of the invention may be better understood in connection with the following examples, which are presented for purposes of illustration and not by way of limitation.

EXAMPLE 1

Isolation and Identification of *Salmonella* spp. from Bovine Feces

Methods

Sample collection. A total of 108 fecal samples were collected in the middle Georgia region from September 2001 though January 2002. Samples were obtained from 28 dairy cattle, 80 beef cattle and five calves between four months and one year of age. Ten grams of feces was collected into Cary Blair with indicator fecal transport system (Corpimex, Miami, Fla.), and immediately transported at 5° C. Samples were stored at 4° C. for 0 to 7 days until use.

*Salmonella* isolation and identification. Each fecal sample (10 g) was preenriched in 90 ml of lactose broth (Becton Dickinson, Sparks, Md.) for 24 hours at 35° C. After preenrichment, 1-ml volumes of enrichment culture were transferred, for selective enrichment, to 10 ml of selenite cystine broth (Becton Dickinson, Sparks, Md.) and incubated for 24 hours at 37° C., to 10 ml of tetrathionate broth (Becton Dickinson, Sparks, Md.) and incubated for 48 hours at 37° C., and to 10 ml of Rappaport-Vassiliadis R10 broth (Becton Dickinson, Sparks, Md.) and incubated for 24 hours at 42° C. After selective enrichment, a 10-μl loopful from each broth was plated in duplicate on to the surface of bismuth sulfite agar (BSA), Hektoen enteric agar (HEA), xylose lysine deoxycholate agar (XLD) and xylose lysine tergitol 4 agar (XLT4) (all Becton Dickinson, Sparks, Md.) plates. Plates were incubated for 24 hours at 37° C. Colonies with typical *Salmonella* spp. morphology were selected from all plates, no more than 10 colonies per plate, and transferred into triple sugar iron agar and lysine iron agar (both Becton Dickinson, Sparks, Md.) slants and incubated for 24 hours at 35° C. All presumptive *Salmonella* isolates were tested by the *Salmonella* latex agglutination assay (Oxoid Ltd., Basingstoke, Hampshire, UK). All isolates positive with the *Salmonella* latex agglutination assay were tested with the API 20E assay (bioMerieux, Hazelwood, Mo.) for biochemical characteristics for the identification of *Salmonella*. Zhao, T. et al., *J. Food Prot.* 65:403-407 (2002). Serotyping was conducted at the U.S. Department of Agriculture-Animal and Plant Health Inspection Service (APHIS) National Veterinary Services Laboratories, Ames, Iowa. Antibiotic resistance profiles were conducted at the U.S. Department of Agriculture-Agricultural Research Service, Athens, Ga.

Results

*Salmonella* spp. were isolated from 10 of 108 fecal samples. All positive samples were from beef cattle over one year of age (Table 1), and were collected from an auction market. Two samples were collected on Oct. 16, 2001, three samples were collected Jan. 15, 2002, and five samples were collected Jan. 29, 2002.

TABLE 1

Serotype, serogroup and antibiotic resistance of *Salmonella* spp. isolates

| Isolate No. | Date isolated | Serotype | Serogroup | Antibiotic resistance[a,b] |
|---|---|---|---|---|
| 55 | Oct. 16, 2001 | Newport | C2 | AAmCeCfCpCSSuT |
| 57 | Oct. 16, 2001 | Newport | C2 | AAmCeCfCpCSSuT |
| 73 | Jan. 15, 2002 | Bareilly | C1 | None |
| 74 | Jan. 15, 2002 | Mbandaka | C1 | None |
| 78 | Jan. 15, 2002 | Newport | C2 | AAmCeCfCpCSTTr |
| 88 | Jan. 29, 2002 | Newport | C2 | AAmCeCfCpCSSuTTr |
| 90 | Jan. 29, 2002 | Montevideo | C1 | None |
| 92 | Jan. 29, 2002 | Meleagridis | E | None |
| 102 | Jan. 29, 2002 | Monophasic | B | None |
| 103 | Jan. 29, 2002 | Monophasic | B | None |

[a] A = ampicillin, Am = amoxicillin/clavulanic acid, Ce = cefoxitin, Cf-ceftiofur, Cp = cephalothin, C = chloramphenicol, S = streptomycin, Su = sulphamethoxazole, T = tetracycline Tr = trimethoprim/sulphamethoxazole
[b] Screened against, amikacin, amoxicillin/clavulanic acid, ampicillin, apramycin, cefoxitin, ceftiofur, ceftriaxone, cephalothin, chloramphenicol, ciprofloxacin, gentamicin, inipenem, kanamycin, nalidixic acid, streptomycin, sulphamethoxazole, tetracycline, trimethoprim/sulphamethoxazole The positive isolates included serogroups B, C1, C2, and E, four of which were serotyped as *Salmonella* Newport, two as monophasic *Salmonella* sp., one as *Salmonella* Bareilly, one as *Salmonella* Mbandaka, one as *Salmonella* Montevideo, and one as *Salmonella* Meleaglidis.

Antimicrobial resistance profiles indicated that all four of the *Salmonella* Newport isolates were resistant to amoxicillin/clavulanic acid, ampicillin, cefoxitin, ceftiofur, cephalothin, chloramphenicol, streptomycin, and tetracycline. Isolates S55 and S57 were additionally resistant to sulphamethoxazole, and isolate S78 was also resistant to trimethoprim/sulphamethoxazole. Isolate S88 was additionally resistant to sulphamethoxazole and trimethoprim/sulphamethoxazole, and had intermediate resistance to ceftriazone. All other *Salmonella* isolates had intermediate resistance to tetracycline, but were sensitive to all other antibiotics. All isolates were sensitive to amikaxin, apramycin, ciprofloxacin, gentamicin, imipenem, kanamycin, and naladixic acid.

EXAMPLE 2

Isolation and Identification of Competitive Inhibition Bacteria

Methods

Isolation of potential competitive inhibition bacteria. *Salmonella*-negative fecal samples were serially diluted (1:10) in 0.1% peptone buffer, 0.1 ml of each dilution was plated in duplicate onto MacConkey agar (MAC) and tryptic soy agar (TSA) (both Becton Dickinson, Sparks, Md.), and the plates were incubated for 24 hours at 37° C. Seven colonies were randomly selected from MAC agar plates, and three colonies were randomly selected from TSA plates. Each colony was transferred to a test tube containing 10 ml of trypic soy broth (TSB) (Becton Dickinson, Sparks, Md.) and incubated for 24 hours at 37° C.

Screening of cultures for anti-*Salmonella Typhimurium* DT104 properties. A three-strain mixture of *Salmonella enteritidis* serovar *Typhimurium* DT104 from our culture collection, including strains 8748A-1 (cattle isolate, R-type ACSSuT), 11942A-1 (cattle isolate, R-type ACSSuT), and 62 (ground beef isolate, R-type ASSuT), were initially used to screen cultures for anti-*Salmonella Typhimurium* DT104 activity. Two methods were used to screen for activity, the disk method (Zhao, T. et al., *J. Clin. Microbiol.* 36:641-647 (1998)) and the agar spot test (Schillinger, U. et al., *Appl. Environ. Microbiol.* 55:1901-1906 (1989)).

Approximately $10^7$ *S. Typhimurium* DT104 cells of approximately equal populations of each strain in 0.1 ml were plated onto the surfaces of XLD and TSA plates and allowed to dry for at least 30 minutes. Supernatant fluid from each culture was filter sterilized (0.2-µl-pore-size cellulose acetate membrane: Nalgene Co., Rochester N.Y.) for determination of anti-*S. Typhimurium* DT104 activity. Two disks (12 mm diameter, Dispens-O-Disc, Difco Laboratories, Detroit, Mich.) were placed on the surface of both the TSA and XLD plates, and 0.1 ml of the filter-sterilized supernatant fluid from a single culture was applied to the surface of the disk. In addition, filter-sterilized supernatant fluid from *E. coli* ATCC 14763 (produces colicin V) and 70% ethanol were used as positive controls, and filter-sterilized TSB was used as the negative control. Cultures were incubated for 24 hours at 37° C. and observed for zones of growth inhibition. Competitive inhibition bacteria were selected as those that produced a clear zone of at least 1 mm around the disk.

Isolates were streaked onto TSA for single colonies and incubated for 24 hours at 37° C. Single colonies were spot inoculated onto TSA and MAC plates and incubated for 24 hours at 37° C. for colony development. Five milliliters of brain heart infusion broth (BHI) (Becton Dickinson, Sparks, Md.) with 0.5% agar (Becton Dickinson, Sparks, Md.) containing approximately $10^6$ CFU of the three strain *S. Typhimurium* DT104 mixture at 50° C. was applied onto the surface of each plate, without disturbing the colony, and allowed to cool. Plates were incubated for 24 hours at 37° C., and observed for zones of growth inhibition. Competitive inhibition bacteria were selected as those that produced a clear zone of at least 1 mm around the disk.

Competitive inhibition cultures were then screened, using the methods described above, against nine additional strains of *S. Typhimurium* DT104, obtained from the collection of P. J. Fedorka-Cray, U.S. Department of Agriculture-Agricultural Research Service, Athens, Ga. All strains were cattle isolates, and included from 1998 strains 526-K, 2848-K and 12993-K, from 1999 strains MH25382, 99-103712-5 and 12-410 and from 2000 strains 4698-K, NE14055, IA45025. Competitive inhibition cultures were screened against 10 *Salmonella* spp. isolates obtained during the screening process of this study.

The pH of TSB was determined before and after culture growth. The pH of TSB and MAC plates was determined before colony growth, and after colony growth, both near the colony and 2 cm away from the colony following 24 hours of growth at 37° C. Growth curves for the competitive inhibition isolates strains and *Salmonella* were performed and generation times were calculated.

Identification of competitive inhibition bacteria. Initially competitive inhibition isolates were characterized by Gram staining. Gram-positive strains were subjected to catalase tests, oxidase tests, and to biochemical testing using the API 50CH Assay (bioMerieux, Hazelwood, Mo.) with both the CHL media for lactic acid bacteria, and the CHB/E media for *Bacillus* spp. Spore formation was determined by holding overnight cultures at 80° C. with agitation at 190 rpm for 10 minutes, then streaking the cultures in duplicate onto TSA plates and incubating for 24 hours at 37° C.

Gram-negative isolates were subjected to biochemical testing using the API 20E Assay (bioMerieux, Hazelwood, Mo.), and subtyping by PFGE using procedures similar to those described previously (Meng, J. et al., *J. Med. Microbiol.* 42:258-263 (1995)) and those used by the Centers for Disease Control and Prevention. This involved growing isolates on TSA plates for 24 hours at 37° C., then suspending cells of each culture in Cell Suspension Buffer (CSB) (100 mM Tris:100 mM EDTA, pH 8.0) with a sterile swab to a cell populations having an optical density of 1.3-1.4 at 610 nm (SPEC). The bacterial suspension, 0.2 ml, was mixed with 10 µl of 20 mg proteinase K/ml and 0.2 ml 1% SeaKem Gold: 1% SDS agarose in TE buffer (1 mM Tris:1 mM EDTA, pH 8.0). The mixture was dispensed into sample moulds and the agarose plugs were digested with 0.1 mg proteinase K/ml in lysis buffer (20 mM Tris:50 mM EDTA, pH 8.0+1% Sarcosine at 54° C. for 2 hours. The plugs were then washed at 50° C., three times in sterile water and three times in TE buffer. Plugs were cut to 2.5 mm wide, prerestricted with 1× restriction buffer for 10 minutes at 37° C., then restricted using 50 U XbaI for 2 hours at 37° C. The reaction was stopped by the removal of reaction buffer and the addition of 0.5×Tris-borate EDTA buffer (TBE). The DNA samples were electrophoresed in 1% SeaKem gold agarose in 0.5×TBE buffer with a contour-clamped homogeneous electric field device (CHEF MAPPER, Bio-Rad, Hercules, Calif.). After electrophoresis for 18 hours at 6.0 V/cm with pulse times of 2.16 to 54.17 seconds, linear ramping and an electric field angle of 120 at 14° C., the gels were stained with ethidium bromide. The bands were visualized and photographed with UV transillumination.

Antibiotic resistance profiles of all unique isolates were obtained using Sensititre gram-positive and gram-negative MIC plates (TREK Diagnostic Systems, Inc. Westlake, Ohio).

Results

Figure 1B:
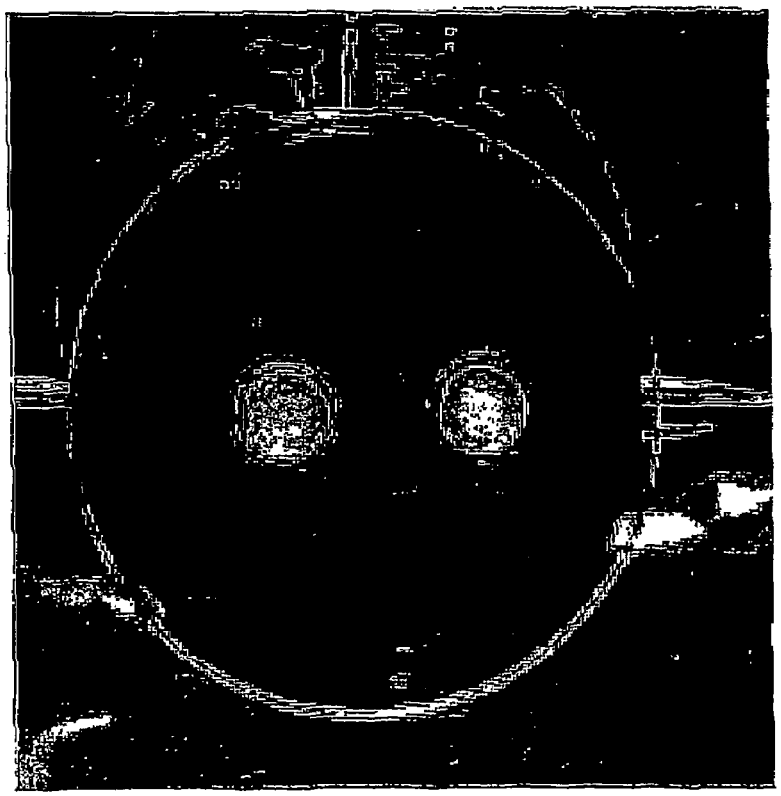
FIG. 1B is a photograph of a paper disk assay showing the zones of inhibition of *S. Typhimurium* DT104 by isolate 36-1 on XLD agar.
Figure 2A:
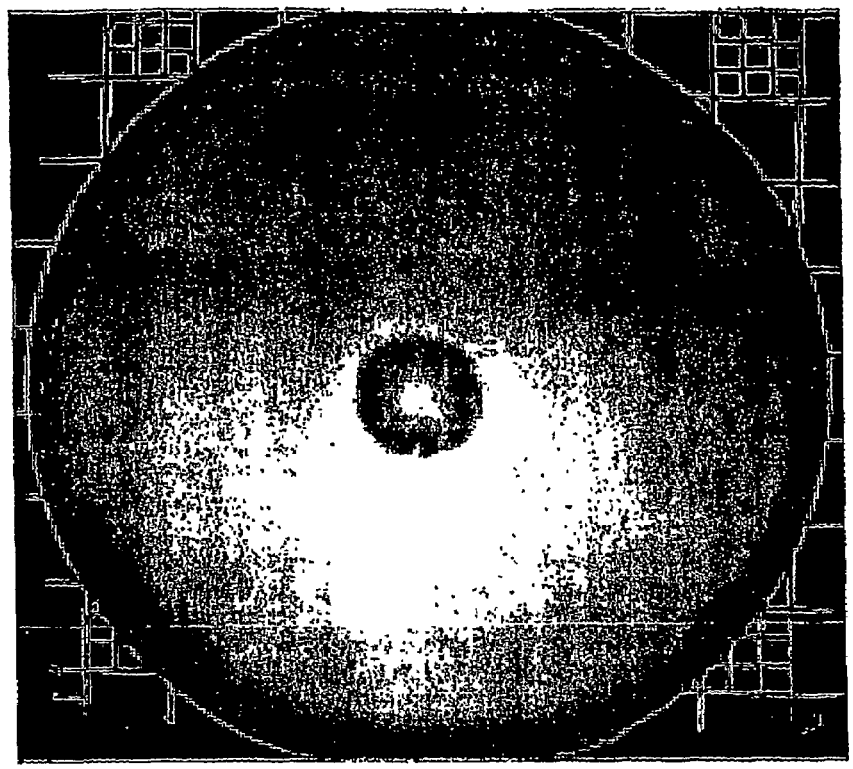
FIG. 2A is a photograph of a agar-spot assay showing the zones of inhibition of *S. Typhimurium* DT104 by isolate 59-9 on TSA agar.
Figure 2B:
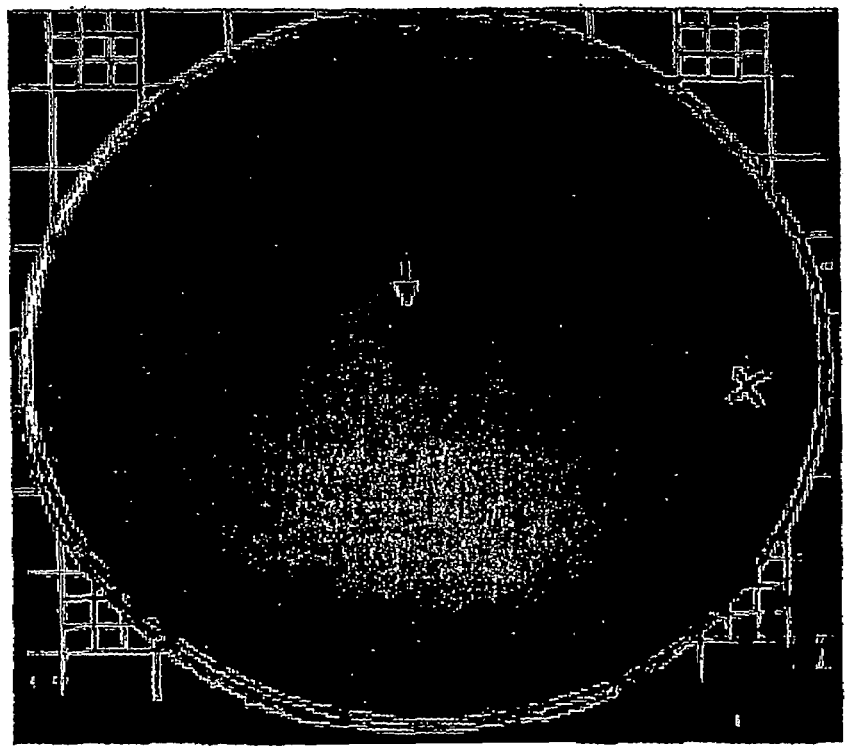
FIG. 2B is a photograph of a agar-spot assay showing the zones of inhibition of *S. Typhimurium* DT104 by isolate 59-9 on MAC agar.

A total of 1097 bacterial colonies were isolated from the feces of cattle determined not to excrete *Salmonella* spp. These bacteria were initially screened for their ability to inhibit the growth of, or kill a three-strain mixture of *S. Typhimurium* DT104 in vitro, and 45 were determined to be inhibitory (Table 2), one through the paper disk assay (FIGS. 1A and 1B.), and 44 via the agar-spot test 9 (FIGS. 2A and 2B.). The size and clarity of the zones of inhibition varied with the type of media and the competitive inhibition candidate.

TABLE 2

Initial screening of potential competitive inhibition bacteria with inhibitory activity against 3 strains of *S. Typhimurium* DT104[a].

| Isolate | | Date of | Disk Assay[b] | | Overlay Assay[c] | |
|---|---|---|---|---|---|---|
| No. | Source | Isolation | XLD | TSA | MAC | TSA |
| 1-1 | Dairy cow | Sep. 10, 2001 | − | − | + | − |
| 3-7 | Dairy cow | Sep. 10, 2001 | − | − | − | + |
| 4-4 | Dairy cow | Sep. 10, 2001 | − | + | + | − |
| 4-5 | Dairy cow | Sep. 10, 2001 | − | − | + | + |
| 5-3 | Dairy cow | Sep. 10, 2001 | − | − | + | − |
| 6-8 | Dairy cow | Sep. 10, 2001 | − | − | − | + |
| 7-7 | Dairy cow | Sep. 10, 2001 | − | − | + | − |
| 8-7 | Dairy cow | Sep. 10, 2001 | − | − | + | − |
| 9-2 | Dairy cow | Sep. 10, 2001 | − | − | + | − |
| 11-1 | Dairy cow | Sep. 10, 2001 | − | − | + | − |
| 12-5 | Dairy cow | Sep. 10, 2001 | − | − | + | − |
| 13-2 | Dairy cow | Sep. 10, 2001 | − | − | + | − |
| 13-6 | Dairy cow | Sep. 10, 2001 | − | − | + | − |
| 15-3 | Dairy cow | Sep. 10, 2001 | − | − | + | − |
| 15-6 | Dairy cow | Sep. 10, 2001 | − | − | + | − |
| 16-2 | Dairy cow | Sep. 10, 2001 | − | − | + | − |
| 16-6 | Dairy cow | Sep. 10, 2001 | − | − | + | − |
| 16-10 | Dairy cow | Sep. 10, 2001 | − | − | + | − |
| 18-4 | Dairy cow | Sep. 10, 2001 | − | − | + | − |
| 18-6 | Dairy cow | Sep. 10, 2001 | − | − | + | − |
| 21-6 | Dairy cow | Sep. 10, 2001 | − | − | + | − |
| 21-9 | Dairy cow | Sep. 10, 2001 | − | − | + | − |
| 23-5 | Dairy cow | Sep. 10, 2001 | − | − | + | − |
| 24-2 | Dairy cow | Sep. 10, 2001 | − | − | + | − |
| 25-10 | Beef calf | Oct. 16, 2001 | − | − | + | + |
| 29-5 | Beef calf | Oct. 16, 2001 | − | − | + | + |
| 30-1 | Beef calf | Oct. 16, 2001 | − | − | + | + |
| 30-5 | Beef calf | Oct. 16, 2001 | − | − | + | + |
| 31-6 | Beef cow | Oct. 16, 2001 | ++ | ++ | − | − |
| 35-3 | Beef cow | Oct. 16, 2001 | − | − | + | − |
| 39-3 | Beef cow | Oct. 16, 2001 | − | − | + | − |
| 44-2 | Beef cow | Oct. 16, 2001 | − | − | + | − |
| 44-4 | Beef cow | Oct. 16, 2001 | − | − | + | − |
| 47-10 | Beef cow | Oct. 16, 2001 | − | − | − | ++ |
| 50-10 | Beef cow | Oct. 16, 2001 | − | − | − | ++ |
| 51-2 | Beef cow | Oct. 16, 2001 | − | − | + | + |
| 58-7 | Beef cow | Oct. 16, 2001 | − | − | + | + |
| 58-9 | Beef cow | Oct. 16, 2001 | − | − | − | ++ |
| 59-9 small | Beef cow | Oct. 16, 2001 | − | − | − | ++ |
| 59-9 big | Beef cow | Oct. 16, 2001 | − | − | − | ++ |
| 66-3 | Beef cow | Jan. 15, 2002 | − | − | + | − |
| 71-8 | Beef cow | Jan. 15, 2002 | − | − | + | +++ |
| 76-9 | Beef cow | Jan. 15, 2002 | − | − | − | ++ |
| 101-1 | Beef cow | Jan. 29, 2002 | − | − | + | + |
| 106-2 | Beef cow | Jan. 29, 2002 | − | − | + | + |

[a]Strains include: 8748A-1, 11942A-1, 62
[b]Zone of inhibition: ++ = >2.0 mm, + = <2.0 mm, −= no zone
[c]Zone of inhibition: +++ = >10 mm, ++ = >5.0 mm, + = <5.0 mm, −= no zone The 45 candidates were screened for in vitro inhibitory activity against an additional nine isolates of *S. Typhimurium* DT104, and 30 were determined to be inhibitory (Table 3 and Table 4), one through the paper disk assay, and 29 through the agar-spot assay. These 30 candidates were then screened for antimicrobial activity against the isolated *Salmonella* spp. isolates from the bovine feces. Only six gram-positive bacteria produced any degree of inhibitory activity against all 10 strains as demonstrated by the agar spot test. Three gram-negative isolates were inhibitory to five of the ten isolated strains (Table 5 and Table 6).

TABLE 3

Screening of potential competitive inhibition bacteria with inhibitory activity against 5 strains of *S. Typhimurium* DT104[a].

| Isolate | Disk Assay[b] | | Overlay Assay[c] | |
|---|---|---|---|---|
| No. | XLD | TSA | MAC | TSA |
| 1-1 | − | − | + | − |
| 3-7 | − | − | + | − |
| 4-4 | − | − | + | − |
| 4-5 | − | − | + | − |
| 5-3 | − | − | + | + |
| 6-8 | − | − | + | − |
| 7-7 | − | − | + | − |
| 8-7 | − | − | − | − |
| 9-2 | − | − | + | − |
| 11-1 | − | − | + | − |
| 12-5 | − | − | + | − |
| 13-2 | − | − | + | − |
| 13-6 | − | − | + | − |
| 15-3 | − | − | + | − |
| 15-6 | − | − | + | − |
| 16-2 | − | − | + | − |
| 16-6 | − | − | + | − |
| 16-10 | − | − | − | − |
| 18-4 | − | − | + | − |
| 18-6 | − | − | + | − |
| 21-6 | − | − | + | − |
| 21-9 | − | − | − | + |
| 23-5 | − | − | + | − |
| 24-2 | − | − | + | + |
| 25-10 | − | − | + | − |
| 29-5 | − | − | + | − |
| 30-1 | − | − | + | − |
| 30-5 | − | − | + | + |
| 31-6 | ++ | ++ | + | − |
| 35-3 | − | − | + | − |
| 39-3 | − | − | − | − |
| 44-2 | − | − | − | − |
| 44-4 | − | − | − | − |
| 47-10 | − | − | − | +++ |
| 50-10 | − | − | − | − |
| 51-2 | − | − | + | − |
| 58-7 | − | − | + | − |
| 58-9 | − | − | − | +++ |
| 59-9 small | − | − | − | +++ |
| 59-9 big | − | − | − | +++ |
| 66-3 | − | − | + | − |
| 71-8 | − | − | − | +++ |
| 76-9 | − | − | − | +++ |
| 101-1 | − | − | + | − |
| 106-2 | − | − | + | − |

[a]Strains include: AI45025, MH2538, 99-103712-5, NE14055, 12-410
[b]Zone of inhibition: ++ = >2.0 mm, + = <2.0 mm, − = no zone
[c]Zone of inhibition: +++ = >10 mm, ++ = >5.0 mm, + = <5.0 mm, − = no zone

TABLE 4

Screening of potential competitive inhibition bacteria with inhibitory activity against 4 strains of *S. Typhimurium* DT104[a].

| Isolate | Disk Assay[b] | | Overlay Assay[c] | |
|---|---|---|---|---|
| No. | XLD | TSA | MAC | TSA |
| 1-1 | − | − | + | − |
| 3-7 | − | − | + | + |
| 4-4 | − | − | + | − |
| 4-5 | − | − | + | − |
| 5-3 | − | − | − | + |
| 6-8 | − | − | + | − |
| 7-7 | − | − | + | − |
| 8-7 | − | − | − | − |

TABLE 4-continued

Screening of potential competitive inhibition bacteria with inhibitory activity against 4 strains of *S. Typhimurium* DT104[a].

| Isolate | Disk Assay[b] | | Overlay Assay[c] | |
|---|---|---|---|---|
| No. | XLD | TSA | MAC | TSA |
| 9-2 | − | − | + | − |
| 11-1 | − | − | + | − |
| 12-5 | − | − | + | − |
| 13-2 | − | − | + | − |
| 13-6 | − | − | + | − |
| 15-3 | − | − | − | + |
| 15-6 | − | − | + | − |
| 16-2 | − | − | + | − |
| 16-6 | − | − | + | + |
| 16-10 | − | − | − | − |
| 18-4 | − | − | + | − |
| 18-6 | − | − | − | − |
| 21-6 | − | − | − | − |
| 21-9 | − | − | − | + |
| 23-5 | − | − | − | − |
| 24-2 | − | − | − | − |
| 25-10 | − | − | − | − |
| 29-5 | − | − | − | − |
| 30-1 | − | − | + | − |
| 30-5 | − | − | + | − |
| 31-6 | ++ | ++ | + | − |
| 35-3 | − | − | + | − |
| 39-3 | − | − | + | − |
| 44-2 | − | − | + | − |
| 44-4 | − | − | − | − |
| 47-10 | − | − | − | +++ |
| 50-10 | − | − | − | − |
| 51-2 | − | − | + | − |
| 58-7 | − | − | + | − |
| 58-9 | − | − | − | +++ |
| 59-9 small | − | − | − | +++ |
| 59-9 big | − | − | − | +++ |
| 66-3 | − | − | + | − |
| 71-8 | − | − | − | +++ |
| 76-9 | − | − | − | +++ |
| 101-1 | − | − | + | + |
| 106-2 | − | − | + | − |

[a]Strains include: 12993-k, 2748-k, 520-k, 4698-k
[b]Zone of inhibition: ++ = >2.0 mm, + = <2.0 mm, − = no zone
[c]Zone of inhibition: +++ = >10 mm, ++ = >5.0 mm, + = <5.0 mm, − = no zone

TABLE 5

Screening of potential competitive inhibition bacteria with inhibitory activity against 5 strains of *Salmonella* spp.[a] isolated from beef cattle in Georgia.

| Isolate | Disk Assay[b] | | Overlay Assay[c] | |
|---|---|---|---|---|
| No. | XLD | TSA | MAC | TSA |
| 1-1 | − | − | − | − |
| 3-7 | − | − | − | − |
| 4-4 | − | − | − | − |
| 4-5 | − | − | − | − |
| 5-3 | − | − | − | − |
| 6-8 | − | − | − | − |
| 7-7 | − | − | − | − |
| 8-7 | − | − | − | − |
| 9-2 | − | − | − | − |
| 11-1 | − | − | − | − |
| 12-5 | − | − | + | − |
| 13-2 | − | − | − | − |
| 13-6 | − | − | − | − |
| 15-3 | − | − | − | − |
| 15-6 | − | − | − | − |
| 16-2 | − | − | − | − |
| 16-6 | − | − | − | − |
| 16-10 | − | − | − | − |
| 18-4 | − | − | − | − |
| 18-6 | − | − | − | − |
| 21-6 | − | − | − | − |
| 21-9 | − | − | − | − |
| 23-5 | − | − | − | − |
| 24-2 | − | − | − | − |
| 25-10 | − | − | − | − |
| 29-5 | − | − | − | − |
| 30-1 | − | − | − | − |
| 30-5 | − | − | − | − |
| 31-6 | ++ | ++ | + | − |
| 35-3 | − | − | − | − |
| 39-3 | − | − | − | − |
| 44-2 | − | − | − | − |
| 44-4 | − | − | − | − |
| 47-10 | − | − | − | +++ |
| 50-10 | − | − | − | − |
| 51-2 | − | − | − | − |
| 58-7 | − | − | − | − |
| 58-9 | − | − | − | +++ |
| 59-9 small | − | − | − | +++ |
| 59-9 big | − | − | − | +++ |
| 66-3 | − | − | − | − |
| 71-8 | − | − | − | +++ |
| 76-9 | − | − | − | +++ |
| 101-1 | − | − | + | − |
| 106-2 | − | − | − | − |

[a]Strains include: S. Newport 55, S. Newport 57, S. Bareilly 73, S. Mbandaka 74, S. Newport 88
[b]Zone of inhibition: ++ = >2.0 mm, + = <2.0 mm, − = no zone
[c]Zone of inhibition: +++ = >10 mm, ++ = >5.0 mm, + = <5.0 mm, − = no zone

TABLE 6

Screening of potential competitive inhibition bacteria with inhibitory activity against 5 strains of *Salmonella* spp.[a] isolated from beef cattle in Georgia.

| Isolate | Disk Assay[b] | | Overlay Assay[c] | |
|---|---|---|---|---|
| No. | XLD | TSA | MAC | TSA |
| 1-1 | − | − | − | − |
| 3-7 | − | − | − | − |
| 4-4 | − | − | − | − |
| 4-5 | − | − | − | − |
| 5-3 | − | − | − | − |
| 6-8 | − | − | − | − |
| 7-7 | − | − | − | − |
| 8-7 | − | − | − | − |
| 9-2 | − | − | − | − |
| 11-1 | − | − | − | − |
| 12-5 | − | − | − | − |
| 13-2 | − | − | − | − |
| 13-6 | − | − | − | − |
| 15-3 | − | − | − | − |
| 15-6 | − | − | − | − |
| 16-2 | − | − | − | − |
| 16-6 | − | − | − | − |
| 16-10 | − | − | − | − |
| 18-4 | − | − | − | − |
| 18-6 | − | − | − | − |
| 21-6 | − | − | − | − |
| 21-9 | − | − | − | − |
| 23-5 | − | − | − | − |
| 24-2 | − | − | − | − |
| 25-10 | − | − | − | − |

TABLE 6-continued

Screening of potential competitive inhibition bacteria with inhibitory activity against 5 strains of Salmonella spp.[a] isolated from beef cattle in Georgia.

| Isolate | Disk Assay[b] | | Overlay Assay[c] | |
|---|---|---|---|---|
| No. | XLD | TSA | MAC | TSA |
| 29-5 | − | − | − | − |
| 30-1 | − | − | − | − |
| 30-5 | − | − | − | − |
| 31-6 | − | − | − | − |
| 35-3 | − | − | − | − |
| 39-3 | − | − | − | − |
| 44-2 | − | − | − | − |
| 44-4 | − | − | − | − |
| 47-10 | − | − | − | +++ |
| 50-10 | − | − | − | − |
| 51-2 | − | − | − | − |
| 58-7 | − | − | − | − |
| 58-9 | − | − | − | +++ |
| 59-9 small | − | − | − | +++ |
| 59-9 big | − | − | − | +++ |
| 66-3 | − | − | − | − |
| 71-8 | − | − | − | +++ |
| 76-9 | − | − | − | +++ |
| 101-1 | − | − | − | − |
| 106-2 | − | − | − | − |

[a]Strains include: S. Newport 88, S. Montevideo 90, S. Meleagridis 92, and monophasic Salmonella spp. 102 and 103.
[b]Zone of inhibition: ++ = >2.0 mm, + = <2.0 mm, − = no zone
[c]Zone of inhibition: +++ = >10 mm, ++ = >5.0 mm, + = <5.0 mm, − = no zone The initial pH of TSB was 7.38, the pH of the medium decreased from 0.82 to 1.70 pH units occurred with the growth of each of the 30 competitive inhibition isolates that were active against all 12 strains of S. Typhimurium DT104. A decrease in pH also occurred with the growth of 12 S. Typhimurium DT104 strains and ranged from 1.10 to 1.37 pH units. The pH on MAC plates either increased slightly or decreased slightly near the competitive inhibition colonies, with a maximum pH increase of 0.22 pH units, and a maximum pH decrease of 0.54 pH units. The pH on TSA plates also increased slightly with the growth of some competitive inhibition candidates and decreased slightly with others, with a maximum pH increase of 0.34 pH units, and a maximum pH decrease of 0.08 pH units.

Generation times of S. Typhimurium DT104 in TSB averaged 25 minutes, those of gram-negative competitive inhibition isolates ranged from 25 minutes to 50 minutes. The generation times of gram-positive competitive inhibition isolates ranged from 38 minutes to 52 minutes.

The six gram-positive bacteria isolates were catalase-positive and oxidase-negative (Table 7). The API 50CH gave only doubtful profiles with the CHL media. With the CHB/E media gave very good identification of isolate 71-8 as Bacillus circulans, good identification of isolates 58-9 and 76-9 as Bacillus circulans, acceptable identification of 47-10 as Bacillus circulans, low discrimination for isolate 59-9 small as Bacillus circulans, and a doubtful profile for 59-9 big as Bacillus circulans. Each isolate was confirmed to be a spore producer. Antibiotic resistance profiles varied, with all strains being resistant to cefoxitin and ceftiofur, some strains being resistant to streptomycin, varying strains having intermediate resistance and resistance to ceftriaxone, all strains having intermediate resistance to tetracycline and some strains having intermediate resistance to chloramphenicol.

TABLE 7

Selected characteristics of potential gram-positive competitive inhibition bacteria with inhibitory activity against 12 strains of S. Typhimurium DT104, and 10 strains of Salmonella spp. isolated from cattle.

| Isolate No. | Identification | Antibiotic resistance[a,b] |
|---|---|---|
| 47-10 | Bacillus circulans | CeCfCtS |
| 58-9 | Bacillus circulans | CeCfCS |
| 59-9 small | Bacillus circulans* | CeCfS |
| 59-9 big | Bacillus circulans* | CeCfS |
| 71-8 | Bacillus circulans | CeCfCtS |
| 76-9 | Bacillus circulans | CeCfS |

Figure 3:
FIG. 3 shows the an agarose gel of the comparison of PFGE DNA pulsotype of gram-negative competitive inhibition isolates from cattle.

[a]Ce = cefoxitin, Cf = ceftiofur, Ct = cefiriaxone, S = streptomycin, C = chloroamphenicol
[b]Screened against, amikacin, amoxicillin/clavulanic acid, ampicillin, apramycin, cefoxitin, ceftiofur, ceftriazone, cephalothin, chloramphenicol, ciprofloxacin, gentamicin, inipenem, kanamycin, nalidixic acid, streptomycin, sulphamethoxazole,tetracycline, trimethoprim/sulphamethoxazole
*Doubtful profiles/low discrimination by API 50 CH screening The 24 gram-negative competitive inhibition (CI) bacteria were identified through biochemical testing using the API 20E Assay (Table 8). Twenty-two E. coli, one Serratia fonticola, and one Enterobacter cloacae were identified. Genomic DNA subtyping revealed 17 different profiles among the 22 E. coli isolates. FIG. 3 shows the resulting electrophoretic pattern of the DNA samples wherein lanes 1 and 8 are E. coli O157:H7, G5244, lane 2 is isolate 5-3, lane 3 is isolate 12-5, lane 4 is isolate 13-6, lane 5 is isolate 13-2, lane 6 is isolate 30-5, lane 7 is isolate 30-1, lane 9 is isolate 15-6, lane 10 is isolate 16-2 and lane 11 is isolate 18-4. Antibiotic resistance profiling revealed that all the strains had some level of resistance to tetracycline. Other resistance to antibiotics varied among strains.

TABLE 8

Selected characteristics of potential gram-negative competitive inhibition bacteria with inhibitory activity against 12 strains of S. Typhimurium DT104 and isolated from cattle.

| Isolate No. | Identification | PFGE DNA subtype[a] | Antibiotic resistance[b,c] |
|---|---|---|---|
| 1-1 | E. coli | Unique | None |
| 3-7 | S. fonticola | Unique | None |
| 4-5 | E. cloacae | Unique | Am, A, Ce, Cp |
| 5-3 | E. coli | Unique | None |
| 6-8 | E. coli | Unique | None |
| 7-7 | E. coli | Unique | None |
| 9-2 | E. coli | Unique | None |
| 11-1 | E. coli | Unique | None |
| 12-5 | E. coli | Same as 5-3 | None |
| 13-2 | E. coli | Unique | SSuT |
| 13-6 | E. coli | Same as 13-2 | SsuT |
| 15-6 | E. coli | Unique | None |
| 16-2 | E. coli | Same as 15-6 | None |
| 16-6 | E. coli | Unique | None |
| 18-4 | E. coli | Same as 15-6 | None |
| 30-1 | E. coli | Unique | Intermediate C |
| 30-5 | E. coli | Same as 30-1 | Intermediate C |
| 31-6 | E. coli | Unique | T |
| 44-2 | E. coli | Unique | Intermediate C |
| 51-2 | E. coli | Unique | None |
| 58-7 | E. coli | Unique | None |
| 66-3 | E. coli | Unique | Su |

TABLE 8-continued

Selected characteristics of potential gram-negative competitive inhibition bacteria with inhibitory activity against 12 strains of S. Typhimurium DT104 and isolated from cattle.

| Isolate No. | Identification | PFGE DNA subtype[a] | Antibiotic resistance[b,c] |
|---|---|---|---|
| 101-1 | E. coli | Unique | A, Cp |
| 106-2 | E. coli | Unique | None |

[a]DNA subtyping as determined by PEGE; unique indicates that the PFGE pulsotype is different from those of the other strains in this study
[b]Am = amoxicillin/clavulancic acid, A = ampicillin, C = chloramphenicol, Ce = cefoxitin, Cp = cephalothin, S = streptomycin, Su = sulphamethoxazole, T = tetracycline
[c]Screened against, amikacin, amoxicillin/clavulanic acid, ampicillin, apramycin, cefoxitin, ceftiofur, ceftriaxone, cephalothin, chloramphenicol, ciprofloxacin, gentamicin, inipenem, kanamycin, nalidixic acid, streptomycin, sulphamethoxazole,tetracycline, trimethoprim/sulphamethoxazole

EXAMPLE 3

Competitive Growth in Feces

Methods

Preparation of competitive inhibition bacteria for inoculation into feces. To facilitate enumeration of the competitive inhibition bacteria, all gram-negative bacterial isolates were selected for resistance to nalidixic acid (50 µg/ml) by exposure to serially (1:2) increased concentrations (0.1, 0.2, 0.4, 0.8, 1.6, 3.2, 6.4, 12.8, 25 and 50 µg/ml) of nalidixic acid in TSB every 24 hours at 37° C. A single colony of each strain of nalidixic acid-resistant, gram-negative, competitive inhibition bacteria was transferred to 10 ml of TSB containing nalidixic acid (50 µg/ml) and incubated for 24 hours at 37° C. A 0.1 ml portion was transferred to 10 ml of TSB and incubated for 16 hours at 37° C. Bacteria were then sedimented by centrifugation (4000×g, 10 min), washed three times in 0.1% phosphate buffered saline, pH 7.2 (PBS) and then resuspended in PBS to an optical density of 0.5 at 640 nm (ca. $10^8$ CFU/ml). Nineteen gram-negative isolates were combined at equal populations. Two levels of inocula ($10^5$ and $10^8$ CFU of gram-negative competitive inhibition isolates strains per g of feces) were used.

Gram-positive competitive inhibition isolates were transferred to 10 ml of TSB and incubated for 16 hours at 37° C. Bacteria were then sedemented by centrifugation (4000×g, 10 min), washed three times in 0.1% phosphate buffered saline, pH 7.2 (PBS) and then resuspended in PBS to an optical density of 0.5 at 640 nm (ca. $10^8$ CFU/ml). Six gram-positive strains were combined at equal populations. Two levels of inocula ($10^5$ and $10^8$ CFU of gram-positive competitive inhibition isolates per g of feces) were used.

A four-strain mixture of S. Typhimurium DT104, including strains 4698-K, 11942A1, 8748A1 and 62, which were previously described, was used. Each strain was grown in 10 ml of TSB held for 16 hours at 37° C. Bacteria were then sedimented by centrifugation (4000×g, 10 min), washed three times in 0.1% phosphate buffered saline, pH 7.2 (PBS) and then resuspended in PBS to an optical density of 0.5 at 640 nm (ca. $10^8$ CFU/ml). The four S. Typhimurium DT104 strains were combined at equal populations. Two levels of inocula ($10^3$ and $10^5$ CFU of S. Typhimurium DT104 per g of feces) were used.

A four strain mixture of Salmonella enteritidis serovar Newport, including, strains S55, S57, S78, and S88, which were all characterized in this study, was used. The four-strain cell suspension was prepared according to the same procedures described above for S. Typhimurium DT104. Two levels of inocula ($10^5$ and $10^8$ CFU of S. Newport per g of feces) were used.

Feces. Ten healthy beef cattle over the age of one year were used as the sources of feces. Fecal samples, which were obtained in June, were collected into 50 ml Falcon tubes, and transported to the laboratory at 5° C. All samples were screened for Salmonella spp. by the procedure described above. All feces were mixed well in stomacher bags at medium speed for 5 minutes.

Inoculation of the feces with S. Typhimurium DT104, S. Newport and competitive inhibition bacteria. The inocula of S. Typhimurium DT104 or S. Newport, and gram-negative competitive inhibition bacteria or gram-positive competitive inhibition bacteria (total 2 ml) mixtures at the appropriate dilution were added to 18 g of feces in sterile stomacher bags and mixed in a stomacher at medium speed for five minutes to obtain the desired bacterial concentrations.

Fecal sample inoculations included, $10^5$ S. Typhimurium DT104/g and $10^8$ gram-negative competitive inhibition bacteria/g, $10^3$ S. Typhimurium DT104/g and $10^5$ gram-negative competitive inhibition bacteria/g, $10^5$ S. Typhimurium DT104/g and $10^8$ gram-positive competitive inhibition bacteria/g, $10^3$ S. Typhimurium DT104/g and $10^5$ gram-positive competitive inhibition bacteria/g, $10^5$ S. Newport/g and $10^8$ gram-positive competitive inhibition bacteria/g, and $10^3$ S. Newport/g and $10^5$ gram-positive competitive inhibition bacteria/g. Controls included both inoculation levels of gram-negative competitive inhibition bacteria, gram-positive competitive inhibition bacteria, S. Typhimurium DT104, S. Newport and total aerobic counts.

Incubation and Sampling. Inoculated fecal samples were held under aerobic conditions at 21° and 37° C. Duplicate samples were obtained at 0, 1, 3, 5, 7, 14 and 21 days post-inoculation. Fecal samples (1 g) were serially diluted (1:10) in 0.1% peptone and assayed for S. Typhimurium DT104 or S. Newport counts by direct plating 0.1 ml portions onto XLD containing ampicillin (32 µg/ml), tetracycline (16 µg/ml) and streptomycin (64 µg/ml) (XLD+). Plates were incubated for 24 hours at 37° C. When Salmonella was not detectable by direct plating, 1 g samples of feces mixed with 0.1% peptone were added to 10 ml of double strength lactose broth for enrichment cultures at 35° C. for 24 hours. Enrichment cultures were subsequently plated onto XLD+ and incubated at 37° C. for 24 hours. Gram-negative competitive inhibition bacteria were enumerated by direct plating 0.1 ml portions onto MAC containing nalidixic acid (50 µg/ml). Plates were incubated for 24 hours at 37° C. Gram-positive competitive inhibition bacteria were enumerated by direct plating 0.1 ml portions onto TSA, incubating for 24 hours at 37° C., and subtracting total aerobic counts obtained for that day of the study. pH values were determined for 1 g fecal samples mixed with 9 ml of 0.1% peptone. All tests were performed in duplicate and the entire study was performed in triplicate.

Statistical analysis. The Statistical Analysis System (SAS) computer statistical package (SAS Institute, Cary, N.C.) was used for analysis of data with Duncan's multiple range tests to determine if significant differences (P<0.05) in populations of S. Typhimurium DT104 exist between mean population values.

Results

Figure 4A:
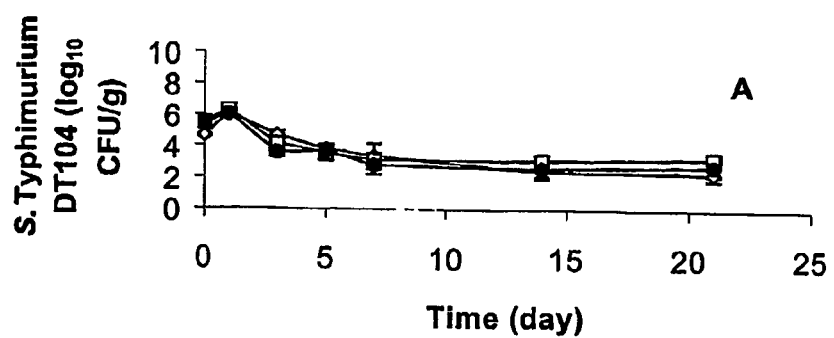
FIG. 4A is a graph showing the growth of *Salmonella* sp. at 37° C. in bovine feces with a low inoculum of DT104 and probiotic bacteria.
Figure 4B:
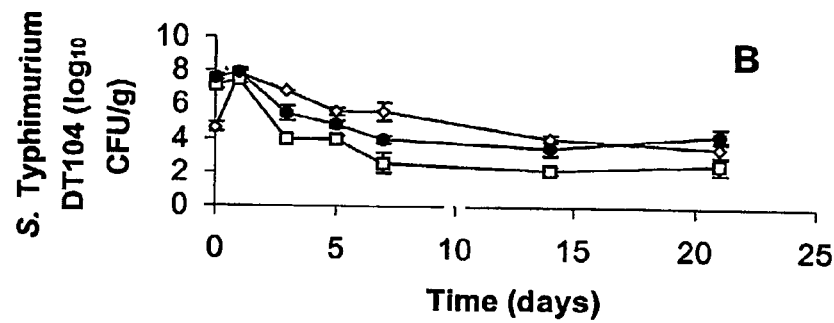
FIG. 4B is a graph showing the growth of *Salmonella* sp. at 37° C. in bovine feces with a high inoculum of DT104 and probiotic bacteria.
Figure 4C:
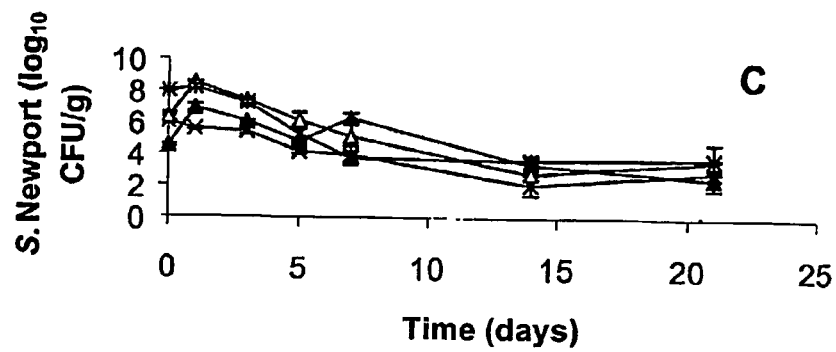
FIG. 4C is a graph showing the growth of *Salmonella* sp. at 37° C. in bovine feces with S. Newport and probiotic bacteria.

The average initial aerobic plate count of the fecal samples was 2.6×$10^9$ CFU/g, and the average initial pH was 7.1. No Salmonella serovars were detected in the feces before inoculation. At 37° C., all the Salmonella populations increased about 2 $\log_{10}$ CFU/g one-day post inoculation (FIGS. 4A-4C, wherein open diamonds represent DT104, closed triangle represent S. Newport, low inoculum and open triangles represent S. Newport, high inoculum). No significant differences were observed with either of the inoculations of competitive inhibition bacteria against *S. Typhimurium* DT104 at both inoculation levels during the 21-day period (FIGS. 4A and 4B, wherein open squares represent DT104 with gram-negative CI bacteria and closed circles represent DT104 with gram-positive CI bacteria). At 37° C., a significant difference ($P>0.05$) was observed with the low-level inoculations of gram-positive competitive inhibition isolates with S. Newport at days 3 and 5, and at the high level inoculation at day 21 (FIG. 4C, wherein x represents S. Newport with gram-positive low inoculum and ζ represents S. Newport with gram-positive high inoculum). The pH of the feces increased slightly (ca. pH of *Salmonella* only=7.25, pH *Salmonella* and CI bacteria=7.58) for all samples during the incubation period.

Figure 5A:
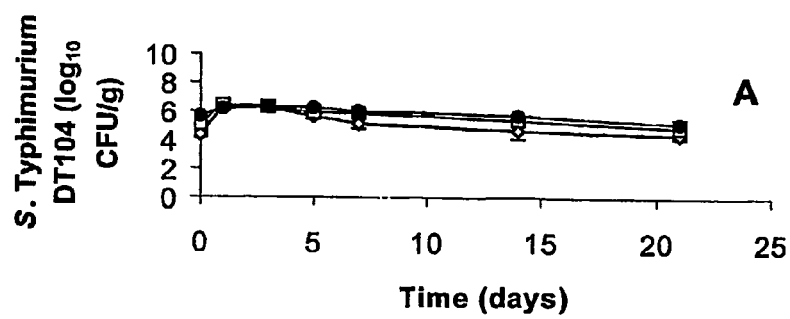
FIG. 5A is a graph showing the growth of *Salmonella* sp. at 21° C. in bovine feces with a low inoculum of DT104 and probiotic bacteria.
Figure 5B:
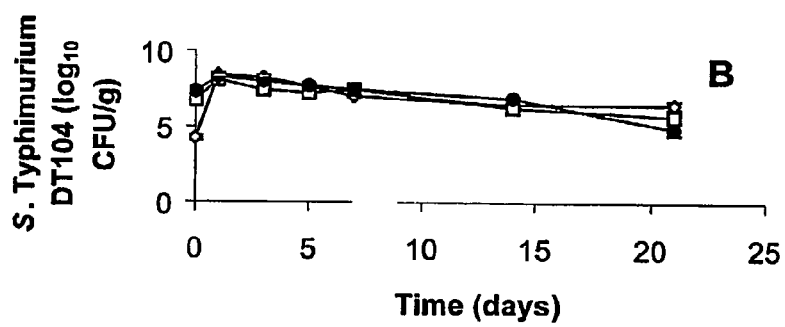
FIG. 5B is a graph showing the growth of *Salmonella* sp. at 21° C. in bovine feces with a high inoculum of DT104 and probiotic bacteria.
Figure 5C:
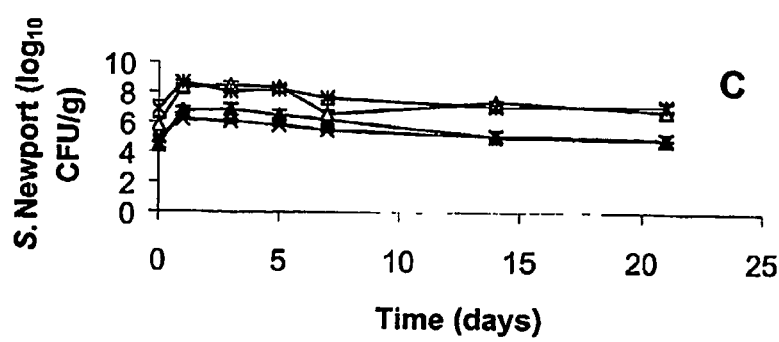
FIG. 5C is a graph showing the growth of *Salmonella* sp. at 21° C. in bovine feces with S. Newport and probiotic bacteria;.

At 21° C., a population increase of 1 to 4 $\log_{10}$ *Salmonella*/g was seen following the first day of growth (FIGS. 5A-5C, wherein open diamonds represent DT104, closed triangle represent S. Newport, low inoculum and open triangles represent S. Newport, high inoculum). The low-level inoculation of gram-negative competitive inhibition bacteria did not significantly reduce ($P>0.05$) *S. Typhimurium* DT104 growth when compared to the control (FIG. 5A, wherein open squares represent DT104 with gram-negative CI bacteria and closed circles represent DT104 with gram-positive CI bacteria). The high inoculation level of gram-negative competitive inhibition bacteria significantly reduced *S. Typhimurium* DT104 populations at day 5 only (FIG. 5B, wherein open squares represent DT104 with gram-negative CI bacteria and closed circles represent DT104 with gram-positive CI bacteria). A significant reduction ($P>0.05$) of *S. Typhimurium* DT104 occurred at day five of the low inoculation level of gram-positive competitive inhibition bacteria. No significant reductions occurred at this temperature with the high inoculation level of gram-positive competitive inhibition bacteria. The gram-positive competitive inhibition bacteria did not significantly reduce ($P>0.05$) the growth/survival of S. Newport at 21° C. (FIG. 5C, wherein x represents S. Newport with gram-positive low inoculum and ζ represents S. Newport with gram-positive high inoculum). The pH increase slightly for all *Salmonella* control samples (ca. pH=7.49), and decreased slightly for *Salmonella* and CI bacteria samples (ca. pH=7.02) during the incubation period.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

What is claimed is:

1. A composition comprising probiotic bacteria, a carrier and an animal's feed, wherein said probiotic bacteria inhibit the growth of *Salmonella* strains and comprise a bacterial isolate selected from the group consisting of isolates 58-9, 76-9 and 31-6, deposited under ATCC Accession Numbers, PTA-5614, PTA-5615 and PTA-5616, respectively.

2. The composition of claim 1 wherein the feed is liquid or solid feed.

3. A probiotic composition that inhibits the growth of *Salmonella* strains, said composition comprising two or more bacterial isolates selected from the group consisting of isolates 58-9, 76-9 and 31-6, deposited under ATCC Accession Numbers, PTA-5614, PTA-5615 and PTA-5616, respectively, and a carrier.

4. The probiotic composition of claim 3 wherein the carrier contains an ingredient that promotes viability of the bacteria during storage.

5. The probiotic composition of claim 3 wherein the composition further comprises animal feed and said bacteria and carrier are combined with the animal feed.

6. The probiotic composition of claim 5 wherein animal feed is selected from the group consisting of liquid feed and solid feed.

7. The probiotic composition of claim 3 wherein the composition is formulated as an inoculant paste.

* * * * *